(12) United States Patent
Yan et al.

(10) Patent No.: US 10,111,811 B2
(45) Date of Patent: Oct. 30, 2018

(54) AIR-COOLING MICRO DROP PILL CAPSULE PRODUCTION LINE

(71) Applicant: TASLY PHARMACEUTICAL GROUP CO., LTD., Tianjin (CN)

(72) Inventors: Xijun Yan, Tianjin (CN); Xiaobing Sun, Tianjin (CN); Yongfeng Zheng, Tianjin (CN); Lijun Fan, Tianjin (CN); Yan Fu, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 309 days.

(21) Appl. No.: 14/903,789

(22) PCT Filed: Jul. 11, 2014

(86) PCT No.: PCT/CN2014/082103
§ 371 (c)(1),
(2) Date: Jan. 8, 2016

(87) PCT Pub. No.: WO2015/003660
PCT Pub. Date: Jan. 15, 2015

(65) Prior Publication Data
US 2016/0166472 A1    Jun. 16, 2016

(30) Foreign Application Priority Data

Jul. 11, 2013 (CN) .......................... 2013 1 0290968

(51) Int. Cl.
*A61J 3/00* (2006.01)
*B01J 2/18* (2006.01)
(Continued)

(52) U.S. Cl.
CPC .................. *A61J 3/005* (2013.01); *A61J 3/06* (2013.01); *B01J 2/02* (2013.01); *B01J 2/04* (2013.01);
(Continued)

(58) Field of Classification Search
USPC .................................................. 425/5, 6, 10
See application file for complete search history.

(56) References Cited

U.S. PATENT DOCUMENTS 3,436,837 A * 4/1969 Wagman .................. F26B 5/06
                                                           159/DIG. 11
4,752,459 A    6/1988 Perrer
(Continued)

FOREIGN PATENT DOCUMENTS

CN    2448361 Y    9/2001
CN    2508752 Y    9/2002
(Continued)

OTHER PUBLICATIONS

Yang et al., CN 101744722 Translation, 2008.*
(Continued)

*Primary Examiner* — Jacob T Minskey
*Assistant Examiner* — Baileigh Kate Darnell
(74) *Attorney, Agent, or Firm* — Lando & Anatasi, LLP (57) ABSTRACT

An air-cooling micro drop pill capsule production line comprises a drop pill system, an air-cooling circulation system and a control system. The drop pill system comprises a molten material tank and a dripper. A vibration apparatus is arranged between the molten material tank and the dripper, and drives the dripper to vibrate up and down. A vibration shear force cuts liquor flowing out from the dripper into drops, and drop pills are formed after the drops fall into the air-cooling circulation system and are cooled. An online monitoring apparatus is arranged on the dripper, and comprises a pulse signal emission mechanism with an emission frequency which is the same as a vibration frequency of the vibration apparatus. The control system controls and regulates a dropping parameter according to a monitoring result of the online monitoring apparatus. The present invention combines vibration dropping, online monitoring and controlling, air cooling, and fluidized drying and coating together, which satisfies the requirement of high-speed dropping, micro pill preparation and improving a drug-loading capacity. Thus, the drug-loading capacity of drop pills can be (Continued)

multiply improved, the usage of auxiliary materials and the dosage can be greatly reduced, organic solvent residual can be completely avoided, and requirements of different processes including slow-release coating, film coating and sugar coating can be satisfied.

19 Claims, 4 Drawing Sheets

(51) Int. Cl.
  *B01J 2/04* (2006.01)
  *B01J 2/02* (2006.01)
  *A61J 3/06* (2006.01)
(52) U.S. Cl.
  CPC .............. *B01J 2/18* (2013.01); *A61J 2200/42* (2013.01); *A61J 2200/44* (2013.01)

(56) References Cited

U.S. PATENT DOCUMENTS

| | | | |
|---|---|---|---|
| 8,568,628 B2* | 10/2013 | Norikane | ............ B01J 2/04 264/13 |
| 2006/0199010 A1* | 9/2006 | DiCarlo | ............ A61K 9/1694 428/402.2 |

FOREIGN PATENT DOCUMENTS

| | | |
|---|---|---|
| CN | 1775204 A | 5/2006 |
| CN | 2794513 Y | 7/2006 |
| CN | 2865683 Y | 2/2007 |
| CN | 101229099 A | 7/2008 |
| CN | 202027925 U | 11/2011 |
| JP | S61-270202 A | 11/1986 |

OTHER PUBLICATIONS

Liu et al., CN 101279220 Translation, 2008.*
Wang et al., CN 102078259 Translation, 2010.*
Zhang et al., CN 202027925 Translation, 2011.*
Li, CN 201200979 Translation, 2008.*
Zhou et al., CN 201589495 Translation, 2010.*
Peng, Y., "Design of Automatic Control System of New Fully-Automatic Pulse Pill Dropping Machine," Pharmaceutical & Engineering Design 2002, 23(5), pp. 40-43.
Yang, M., "Pill Dropping Machine," p. 227 (undated).
Office Action in corresponding JP2016-524677, dated Mar. 20, 2018.

* cited by examiner

AIR-COOLING MICRO DROP PILL CAPSULE PRODUCTION LINE

CROSS-REFERENCE TO RELATED APPLICATIONS

This application is a U.S. national stage application and claims the benefit under 35 U.S.C. § 371 of PCT/CN2014/082103, titled AIR-COOLING DROP PILL PRODUCTION LINE, filed Jul. 11, 2014, which claims priority to Chinese Patent Application No. 201310290968.8, filed Jul. 11, 2013, titled AIR-COOLING DROP PILL PRODUCTION LINE, which patent applications are hereby incorporated herein by reference in their entireties for all purposes.

FIELD OF THE INVENTION

The present invention relates to a drop pill machine manufacturing technology, and more specifically, to an air-cooling micro drop pill capsule production line.

BACKGROUND OF THE INVENTION

Drop pill is a kind of traditional dosage form of Chinese medicine preparations, which is widely accepted due to its advantages such as a short production cycle, a rapid onset of action, a high drug stability and a portable storage.

The existing drop pill production methods are generally a method of natural dropping combined with liquid cooling, or a method of pressurized dropping which is developed from the natural dropping combined with liquid cooling. The disadvantages of the existing apparatus are as follows: (1) according to a characteristic of liquid cooling medium, a range of pill weights of drop pills dropped in this cooling manner is limited, i.e., pill weights are generally 20~30 mg, whereas neither micro pills nor large pills can be dropped; (2) meanwhile, in order to ensure a dropping effect, it is necessary to add a lot of matrix into a raw material of liquor, resulting in a small drug-loading capacity per unit and a correspondingly increased dosage; (3) furthermore, when the liquid cooling manner is used, a liquid-solid separation for separating drop pills from cooling liquid is necessary, but it is difficult to perform a complete separation between them, and thus the cooling liquid residue inevitably occurs on the drop pills and the drop pills are polluted; (4) when a yield is required to be adjusted, the traditional dropping apparatus commonly can adjust it only by changing a dripper and a pressure, hence a dropping frequency is low; in addition, the apparatus needs a large heat-exchange surface area of paraffin, thus a cycle efficiency is low and a power consumption is high, accordingly, the apparatus has a large volume, which likely possesses dead spots inaccessible to a clean process and a possible risk of cross contamination.

At present, a development trend and a research direction for improving the drop pill apparatus are how to improve the existing dropping apparatus in terms of improving its stability in a dropping process, efficiently increasing a formation quality of the drop pills, improving the production speed and the drug-loading capacity, and widening a range of droppable sizes of the drop pills, while reducing power consumption and the usage of cooling liquid as well as preventing the drop pills from pollution.

SUMMARY OF THE INVENTION

Problems to be Solved

In view of the disadvantages in the related art, the present invention aims to provide an air-cooling micro drop pill capsule production line, which pioneers a combination of vibration dropping, online monitoring and controlling, air cooling, and fluidized drying and coating, and which can apply to a drop pill preparation and a drop pill capsule preparation. This production line satisfies the requirements of high-speed dropping, ability of micro pill preparation and improving drug-loading capacity when producing drop pills, to multiply improve the drug-loading capacity of the drop pills, and to greatly reduce the usage of auxiliary materials and the dosage. The present invention can simplify the operation processes, and can completely avoid any organic solvent residual. The present invention can satisfy requirements of different processes including slow-release coating, film coating and sugar coating. The present invention really achieves low power consumption, high speed, high efficiency and high drug-loading capacity, and thus has a wider droppable range.

Solutions to the Problems

The problems to be solved by the present invention are settled by the following technical solutions.

An air-cooling micro drop pill capsule production line comprises a drop pill system, an air-cooling circulation system and a control system, wherein the drop pill system comprises a molten material tank and a dripper connected thereto, a vibration apparatus which drives the dripper to vibrate up and down is arranged between the molten material tank and the dripper. A generated vibration shear force cuts liquor flowing out from the dripper into drops, and drop pills are formed after the drops fall into the air-cooling circulation system and are cooled. In the production line, an online monitoring apparatus is arranged on the dripper, and comprises a pulse signal emission mechanism with an emission frequency which is the same as a vibration frequency of the vibration apparatus. The control system controls and regulates a dropping parameter according to a monitoring result of the online monitoring apparatus.

As required, the online monitoring apparatus is provided on a lower side face of the dripper; the pulse signal emission mechanism is a stroboscopic lamp with the emission frequency which is the same as the vibration frequency of the vibration apparatus, i.e., 50~300 HZ. In order to observe and record, the online monitoring apparatus further includes a camera arranged corresponding to the stroboscopic lamp, the camera is positioned on the same horizontal plane as the stroboscopic lamp and forms an angle of 15°~145° with an illumination path of the stroboscopic lamp.

To prevent a blockage in a dropping process, the dripper mainly comprises a dropping plate on which a plurality of drip holes are provided, and a concave annular groove is arranged at the periphery of the drip hole. The concave annular groove has an inner diameter equaling to an inner diameter of the drip hole plus 0.4 mm, an outer diameter of 1.5 mm or larger, and a depth of 0.5~5 mm.

The dropping parameters mainly comprise: the emission frequency of the stroboscopic lamp and the vibration frequency of the vibration apparatus: 50~300 HZ, preferably 90~200 Hz, most preferably 130~140 HZ; a dropping speed: 10~40 Kg/hr, preferably 12~30 Kg/hr, most preferably 15~25 Kg/hr; a dropping acceleration: 1~20 G, preferably 3~10 G, most preferably 3.5~4.5 G; a dropping pressure: 0.5~4.0 Bar, preferably 1.0~3.0 Bar, most preferably 1.8 Bar; the dripper's temperature: 70~200° C., preferably 70~100° C., most preferably 75~85° C.

The air-cooling circulation system comprises a cooling duct and a refrigerating apparatus connected to the cooling duct and refrigerating the cooling duct. An interlayer is arranged outside the cooling duct, the lower part of the interlayer communicates with the interior of the cooling duct. The refrigerating apparatus comprises a cooling air refrigerating apparatus and a cold trap refrigerating apparatus. The cooling air refrigerating apparatus comprises a freezer, an air outlet of which and a cooling air inlet of the cooling duct being communicated with each other such that the cooling air rises circularly in an inner chamber of the cooling duct. The cold trap refrigerating apparatus comprises: a refrigerant storage tank containing the refrigerant, a refrigerator refrigerating the refrigerant in the refrigerant storage tank, and a heat exchanger. A refrigerant outlet of the refrigerant storage tank is connected to a refrigerant inlet arranged on the upper part of the interlayer such that the refrigerant is transferred into the interlayer through the refrigerant inlet, then transferred from the upper part of the interlayer to the lower part of the interlayer and then to the inner chamber of the cooling duct. The refrigerant rises circularly together with the cooling air in the inner chamber of the cooling duct simultaneously, and then are discharged or recycled through the top of the cooling duct.

To save energy and prevent pollution due to the harmful refrigerant, the air-cooling circulation system further comprises a gas recycling apparatus including a first valve, a second valve, a gas recycling machine and a separator. One end of a duct controlled by the first valve communicates with the cooling duct, and the other end thereof communicates with atmosphere. One end of a duct controlled by the second valve communicates with the cooling duct, and the other end thereof is connected to the separator via the gas recycling machine. The gas recycling machine further includes a gas discharging pipe, a vortex blower, a gas recycling pipe and a gas recycling box. When the second valve is opened, the vortex blower operates to extract the gas in the cooling duct through the gas discharging pipe, and to discharge the gas collected by extraction into the gas recycling box through the gas recycling pipe.

In order to ensure a good cooling effect, the cooling duct is a straight barrel-shaped or spiral-shaped duct with a length of 5~10 m, preferably 6 m.

To keep clean, an online cleaning device is arranged on the cooling duct and comprises a cleaning unit, a controlling unit, a lifting driving unit and a lifting unit. The controlling unit drives the lifting unit with the lifting driving unit so as to drive the cleaning unit to move up and down. The lifting unit is arranged outside the top of the cooling duct in the air-cooling circulation system. The lifting unit comprises a cleaning unit support frame, a cleaning duct, a cleaning duct support frame, a cleaning duct accommodating plate and a sealing connection pipe. The cleaning duct support frame allows the cleaning duct to extend into the interior of the cooling duct. The cleaning unit support frame includes a plurality of support wheels each abutting against an inner sidewall of the cooling duct. The cleaning unit is connected to one end of the cleaning duct extending into the interior of the cooling duct, and is moved up and down along the center of the cooling duct by the cleaning unit support frame. One end of the sealing connection pipe is connected with the other end of the cleaning duct, to guide a cleaning fluid into the cleaning duct. The lifting unit further comprises an online monitoring apparatus which includes an image capturing unit and a calculating unit. The image capturing unit is arranged on the cleaning unit and used to capture a real-time image in the cooling duct and transmit an image signal to the calculating unit. The calculating unit converts the image signal into a numerical value and compares it with a threshold value, and if the numerical value is higher than the threshold value, a driving signal is transmitted to the controlling unit so as to drive the cleaning unit to perform a cleaning process.

Furthermore, the air-cooling micro drop pill capsule production line further comprises a fluidized drying and coating system, which mainly includes a fluidized bed. An end of the cooling duct is connected to an inlet of the fluidized bed via a vacuum duct. The uncoated drop pills subjected to an air-cooling formation are loaded under vacuum and transferred into the fluidized bed to be dried in a fluidized state and coated. The fluidized bed comprises a furnace body at the lower part of which a material feeding inlet is provided. Below the feeding inlet, an airflow distribution board is provided. The bottom of the airflow distribution board is communicated with an air-out duct of a room-temperature and low-humidity air supply system for supplying a room-temperature and low-humidity air into the furnace body of the fluidized bed via the air-out duct. A fluidized drying process is performed on the materials inside the furnace body. The room-temperature and low-humidity air supply system comprises a housing on which an air-in duct and the air-out duct are provided and a low-humidity assembly arranged in the housing. Air is subjected to a process by the low-humidity assembly after flowing into the housing from the air-in duct, and then is input into the furnace body through the air-out duct. The low-humidity assembly consists of a plurality of devices in series, successively including a dust removal device, a humidity removal device, an air supply device, a heating device, a filtering device and an efficient filtering device along a flowing direction of the airflow. The room-temperature and low-humidity air supply system further comprises an air return duct for recycling the airflow, two ends of the air return duct being connected to the furnace body and the housing, respectively.

As required, a drying temperature of the fluidized bed is in a range of $-20°$ C.~$100°$ C., and a drying time thereof is in a range of 1~4 hours. Further, the fluidized bed preferably uses a drying method of a gradiently-increased temperature, in which the drop pills are fluidized at $-20$~$30°$ C., dried at $15$~$35°$ C. for 10~120 min, dried at $35$~$55°$ C. for 10~60 min, and then dried at $55$~$100°$ C. for 0~60 min. Still further, the fluidized bed uses the drying method of a gradiently-increased temperature, in which most preferably the drop pills are fluidized at $0$~$20°$ C., dried at $25°$ C. for 60 min, dried at $45°$ C. for 30 min, and then dried at $55°$ C. for 0~30 min.

In order to detect the moisture content effectively, an online detecting apparatus for monitoring the moisture content and the distribution of particle sizes of the micro pills is further arranged in the fluidized bed.

Advantageous Effects of the Invention

From above, the present invention combines vibration dropping, online monitoring and controlling, air cooling, and fluidized drying and coating together, and applies to a drop pill preparation and a drop pill capsule preparation. The present invention satisfies the requirements of high-speed dropping, ability of micro pill preparation and improving the drug-loading capacity when producing drop pills, to multiply improve the drug-loading capacity of the drop pills, and to greatly reduce the usage of auxiliary materials and the dosage. The present invention can simplify the operation processes, and can completely avoid any organic solvent residual. The present invention can satisfy requirements of different processes including slow-release coating, film coating and sugar coating. The present invention really achieves low power consumption, high speed, high efficiency and high drug-loading capacity, and thus has a wider droppable range.

Hereinafter, the embodiments for carrying out the present invention will be described in detail in conjunction with the accompanying drawings and the specific examples.

DESCRIPTION OF EMBODIMENTS

Figure 1:
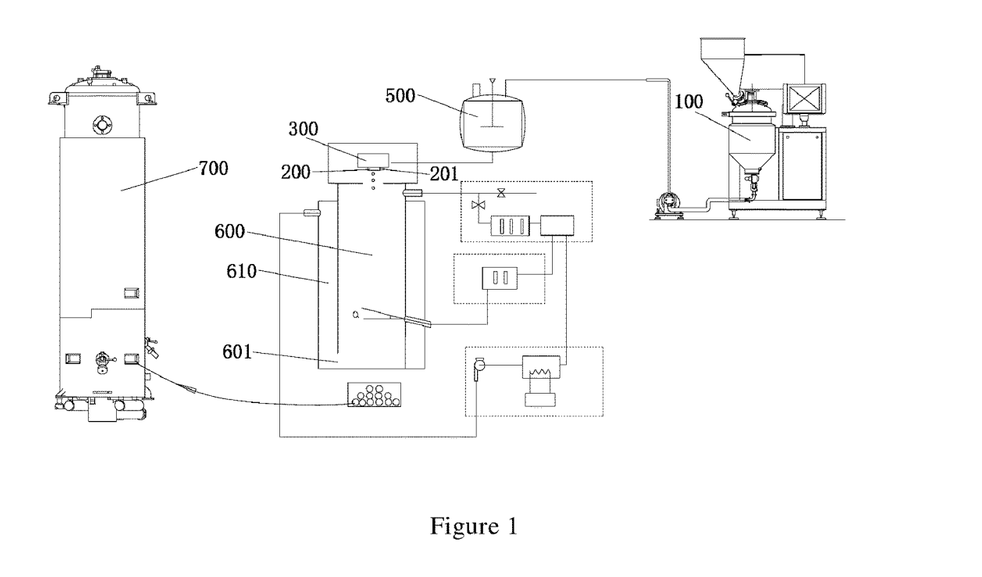
FIG. 1 is a schematic diagram of an overall structure of the invention.

FIG. 1 is a schematic diagram of an overall structure of the present invention. As illustrated in FIG. 1, the present invention provides an air-cooling micro drop pill capsule production line comprising a drop pill system, an air-cooling circulation system and a control system. The drop pill system comprises a molten material tank 100 and a dripper 200 connected thereto, and a vibration apparatus 300 is arranged between the molten material tank 100 and the dripper 200. The vibration apparatus drives the dripper to vibrate up and down, such that the generated vibration shear force cuts liquor flowing out from the dripper into drops, and drop pills are formed after the drops fall into the air-cooling circulation system and are cooled. An online monitoring apparatus is arranged on the dripper, and comprises a pulse signal emission mechanism with an emission frequency which is the same as a vibration frequency of the vibration apparatus. The control system controls and regulates a dropping parameter according to a monitoring result of the online monitoring apparatus. The dropping parameters include: the emission frequency of the stroboscopic lamp and the vibration frequency of the vibration apparatus: 50~300 HZ, preferably 90~200 Hz, most preferably 130~140 HZ; a dropping speed: 10~40 Kg/hr, preferably 12~30 Kg/hr, most preferably 15~25 Kg/hr; a dropping acceleration: 1~20 G, preferably 3~10 G, most preferably 3.5~4.5 G; a dropping pressure: 0.5~4.0 Bar, preferably 1.0~3.0 Bar, most preferably 1.8 Bar; the dripper's temperature: 70~200° C., preferably 70~100° C., most preferably 75~85° C.

As required, the online monitoring apparatus is arranged on a lower side face of the dripper. The pulse signal emission mechanism is a stroboscopic lamp 201 with the emission frequency which is the same as the vibration frequency of the vibration apparatus. In order to observe and record, the online monitoring apparatus may further comprise a camera (not shown in the figure) arranged corresponding to the stroboscopic lamp. The camera is positioned on the same horizontal plane as the stroboscopic lamp, and forms an angle of 15° to 145° with an illumination path of the stroboscopic lamp.

That is, the vibration dropping employed by the present invention is mainly to apply pressure on molten liquor and transfer the molten liquor to the dripper. It makes the dripper vibrate up and down at a preset frequency, waveform and amplitude by using a magnetic/electrodynamic or pneumatic vibration principle. The vibration shear force acts on a liquid column and liquid drops are formed. In general, the vibration frequency is in a range of 50~300 Hz. As required, a magnetic or electrodynamic vibration mode may be used. Such a mode has a characteristic of high vibration frequency and small vibration amplitude, and is suitable for high-speed dropping of a material of low viscosity. Generally, in a pneumatic vibration mode, the vibration frequency and the vibration amplitude are large. The electrodynamic vibration mode is incapable of effectively cutting a material if the material has a viscosity exceeding 800 cp (centipoises). The pneumatic vibration mode may be used in a case that the dripper is blocked and the preparation of drop pills is affected.

To eliminate an influence of a pressure pulse due to the surge of the material liquid on the dropping process in a material liquid transferring process, and to ensure a stable feeding of the material, a buffer tank 500 is further arranged between the molten material tank 100 and the dripper 200. The buffer tank 500 is provided with a compressed air inlet which is connected to an air pump via a pressure duct. A pressure regulating valve is arranged on the pressure duct, to keep the liquor inside the buffer tank to be supplied under a constant pressure. The buffer tank is provided with the following components: a liquid level meter for controlling the feeding speed; a thermal insulation layer, which uses a water bath, an oil bath and an electric heat tracing mode to achieve thermal insulation; a temperature sensor for monitoring the material liquid temperature; and a stirring paddle which can adjust a stirring speed in the buffer tank. Sensors in the buffer tank each may be configured to be a contact type or a non-contact type. A heat-resistant material such as 304, 316L or others that can directly contact a product may be used as the material of the tank body.

Figure 2:
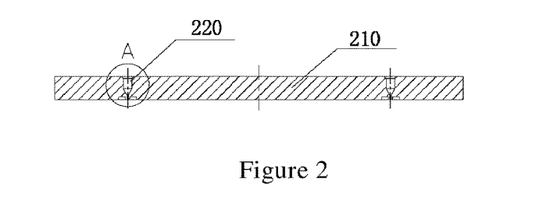
FIG. 2 is a sectional diagram of a dropping plate of the invention.
Figure 3:
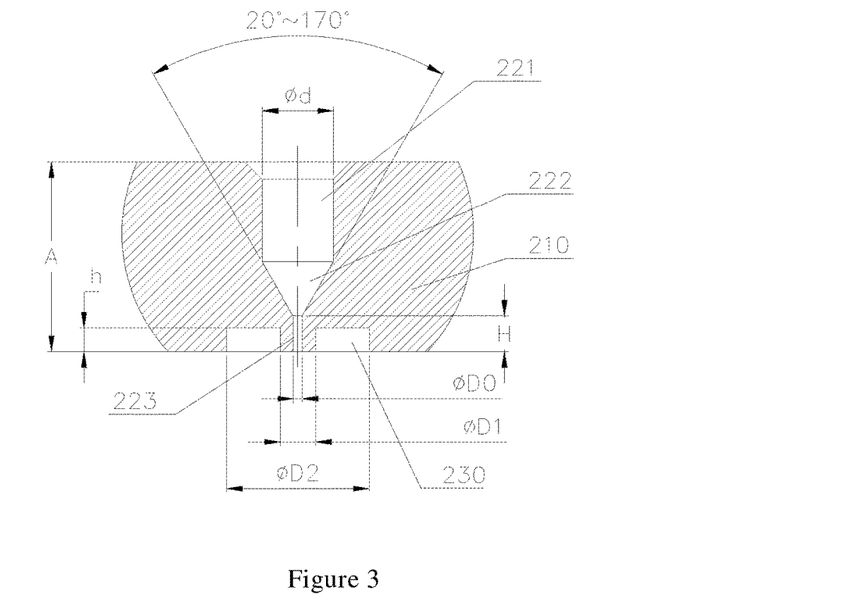
FIG. 3 is an enlarged diagram of a partial structure indicated by A in FIG. 2.

FIG. 2 is a sectional diagram of a dropping plate of the present invention, and FIG. 3 is an enlarged diagram of a partial structure indicated by A in FIG. 2. As illustrated in FIG. 2 and FIG. 3, the dripper 200 of the present invention mainly comprises a dropping plate 210 on which a plurality of drip holes 220 are provided, and the drip holes 220 are arranged at equal intervals along a peripheral direction of the dropping plate 210. As illustrated in FIG. 3, the drip hole 220 consists of a cylindrical cavity 221, a tapered cavity 222 and a straight pipe cavity 223, and the liquid drops drop from an end of the straight pipe cavity 223. On a side face of the dropping plate 210 facing a cooling tank 600, a concave annular groove 230 is arranged at the periphery of an outlet of the straight pipe cavity 223. Since an aperture $D0$ of the outlet of straight pipe cavity 223 is usually 0.1~5 mm, the concave annular groove 230 has an inner diameter $D1=D0+0.4$ mm, an outer diameter $D2$ of 1.5 mm or larger, and a depth h of 0.5 to 5 mm. Additionally, a diameter d of the cylindrical cavity 221 is 0.5~1 mm, a cone angle of the tapered cavity 222 is 20°~170°, a total thickness A of the dropping plate 210 is 6 mm, a height of the straight pipe cavity 223 is $H=(0.5~6)D0$. By providing the concave annular groove 230 at the periphery of the drip hole 220, it is possible to prevent the residual liquor from accumulating around the drip hole 220 when a viscous liquid is ejected at a high speed such that the drip hole 220 is blocked or the dropping is affected eventually.

The dripper 200 may be exposed directly; or alternatively, in order to keep the liquor's temperature constant, a thermal insulation cavity may be arranged outside the dripper, to maintain the dripper's temperature at about 70~200° C. An outer layer of the thermal insulation cavity is provided with a heat insulation material, and an inner layer thereof is provided with a steam heating device or an infrared heating device, so as to avoid a change in viscosity of the liquor due to a temperature change which would influence the effect of dropping. An opening is arranged below the thermal insulation cavity, the location of the opening corresponding to the location of the outlet of the dripper, and the size of the opening corresponding to the width of the dripper. The interior of the thermal insulation cavity may be designed to have a certain arc angle, which makes the dead spots less than those of a square cavity and the cleaning process easier. A lower end of the thermal insulation cavity is opened to ensure a normal falling of drop pills.

Meanwhile, below a side of the dripper 200, a stroboscopic lamp 201 is configured to monitor the dropping situation of drop pills. By using a synchronization stroboscopic principle, an operator can observe a high-speed falling state in real time merely by a visual manner. Of course, in order to observe and record, a real-time monitoring may be performed on the images by a camera. By dropping at a certain vibration frequency such as a vibration frequency of 50 Hz or larger, it is possible to realize a real-time monitoring and an accurate adjustment of the dropping state with reference to appearance of the drop pills. That is, at the same time of a dropping process, a vibration waveform is used as a monitoring index of a PAT monitoring system, and it is possible to measure the distribution of the particle sizes of the drop pills and to monitor the fluidized state of the drop pills in real-time by using a stroboscopic device. By adjusting the vibration parameters, the drug-loading capacity is increased by 50% or higher, and the auxiliary materials are greatly reduced. By adjusting the vibration parameters, the diameters of the drop pills are adjusted in a range of 0.2 mm~3 mm, and it is possible to produce small-sized Chinese medicine dropping micro pills which can better satisfy a capsule filling requirement. The stroboscopic real-time examination and the online monitoring technology employed by the present invention enables the production yield of the drop pills to be increased from a traditional 70% to 95% or higher.

In conjunction with FIG. 1, the air-cooling circulation system of the present invention includes a cooling duct 600, and a refrigerating apparatus connected to the cooling duct 600 and refrigerating the cooling duct. The cooling duct 600 is arranged right under the dripper 200 of the drop pill apparatus, and may be a straight barrel-shaped or spiral-shaped duct. As required, a length of the cooling duct 600 is 5 m~10 m, preferably 6 m. An interlayer 610 is arranged outside the cooling duct 600, a lower part of the interlayer 610 communicates with the interior of the cooling duct 600 via a communicating opening 601.

Figure 4:
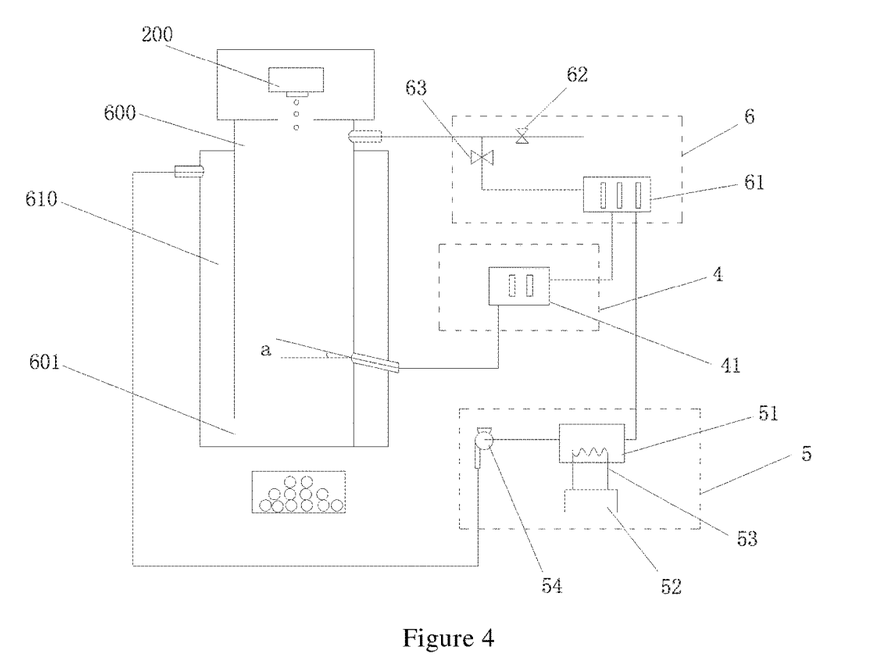
FIG. 4 is a schematic diagram of a structure of a refrigerating apparatus in the invention.

FIG. 4 is a schematic diagram of a structure of a refrigerating apparatus of the present invention. As illustrated in FIG. 4, the refrigerating apparatus comprises a cooling air refrigerating apparatus 4 including a freezer 41. An air outlet of the freezer 41 and a cooling air inlet of the cooling duct 600 are communicated with each other such that the cooling air rises circularly in an inner chamber of the cooling duct 600. Moreover, an angle of 0° to 90° is formed between the cooling air inlet of the cooling duct 600 and the horizontal plane. To further realize a rapid cooling, the refrigerating apparatus also comprises a cold trap refrigerating apparatus 5 including a refrigerant storage tank 51 containing the refrigerant, a refrigerator 52 refrigerating the refrigerant in the refrigerant storage tank 51, and a heat exchanger 53. A refrigerant outlet of the refrigerant storage tank 51 is connected to a refrigerant inlet arranged on the upper part of the interlayer 610 via a pump 54. The refrigerant is transferred into the interlayer 610 through the refrigerant inlet, transferred from the upper part of the interlayer 610 to a lower part of the interlayer 610, and then transferred into the inner chamber of the cooling duct 600. The refrigerant rises circularly together with the cooling air in the inner chamber of the cooling duct 600 simultaneously, and the refrigerant and the cooling air are discharged or recycled through a gas recycling apparatus 6 connected to the top of the cooling duct 600. In general, nitrogen, argon, carbon dioxide or the like is used as the refrigerant.

Figure 5:
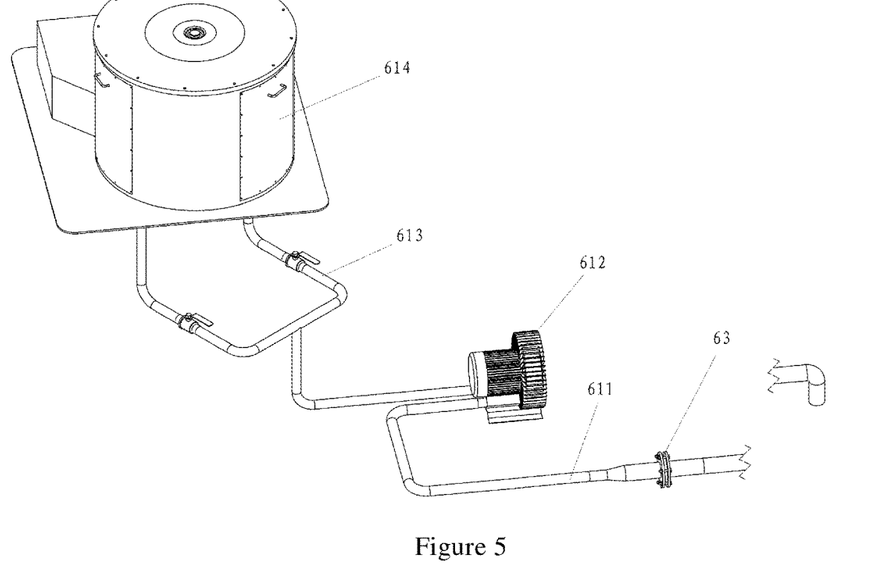
FIG. 5 is a schematic diagram of a structure of a gas recycling apparatus in the invention.

FIG. 5 is a schematic diagram of a structure of a gas recycling apparatus of the present invention. As illustrated in FIG. 4 and FIG. 5, specifically, the gas recycling apparatus 6 comprises a gas recycling machine 61, a first valve 62, a second valve 63 and a separator 64. One end of a duct controlled by the first valve 62 communicates with the cooling duct 600, and the other end thereof communicates with atmosphere. One end of a duct controlled by the second valve 63 communicates with the cooling duct 600, and the other end thereof is connected to the separator 64 via the gas recycling machine 61. As illustrated in FIG. 5, the gas recycling machine 61 includes a gas discharging pipe 611, a vortex blower 612, a gas recycling pipe 613 and a gas recycling box 614. When the second valve 63 is opened, the vortex blower 612 operates to extract the gas in the cooling duct 600 through the gas discharging pipe 611, and discharges the gas collected by extraction into the gas recycling box 614 through the gas recycling pipe 613. The separator 64 is connected to the gas recycling box 614.

When the refrigerant is a harmless gas, the first valve 62 is opened while the second valve 63 is closed, such that the refrigerant and the cooling air in the inner chamber of the cooling duct 600 circularly rise at the same time to the top of the cooling duct 600 and discharged into the atmosphere through the duct communicating with the first valve 62. In contrast, when the refrigerant is a harmful gas, the first valve 62 is closed while the second valve 63 is opened, such that the refrigerant and the cooling air in the inner chamber of the cooling duct 600 circularly rise at the same time to the top of the cooling duct 600 and recycled to the gas recycling machine 61 through the duct communicating with the second valve 63, subsequently, the refrigerant and the cooling air are separated from each other by the separator 64, and then the separated cooling air and refrigerant are transferred to the freezer 41 and the refrigerant storage tank 51, respectively.

Figure 6:
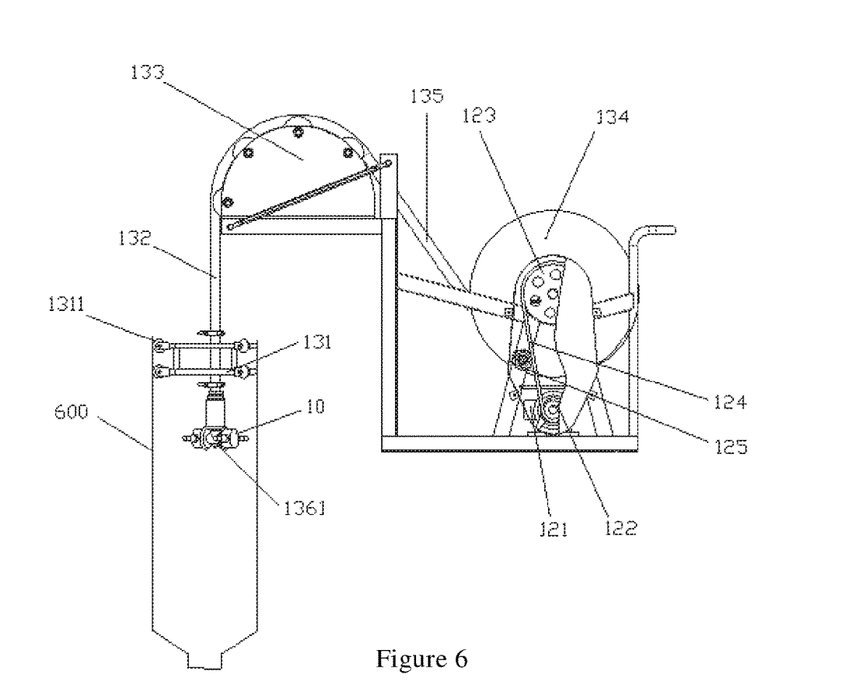
FIG. 6 is a schematic diagram of an overall structure of an online cleaning device of the invention.

FIG. 6 is a schematic diagram of an overall structure of an online cleaning device of the present invention. As illustrated in FIG. 6, in order to keep clean, the air-cooling micro drop pill capsule production line further comprises an online cleaning device including a cleaning unit 10, a cleaning monitoring and controlling unit, a lifting driving unit and a lifting unit. The cleaning unit 10 is a spray header or a spray header with a cleaning cloth. The cleaning monitoring and controlling unit drives the lifting unit with the lifting driving unit so as to drive the cleaning unit 10 to move up and down inside the cooling duct 600. The lifting unit is arranged outside the top of the cooling duct 600. Herein, the lifting unit comprises a cleaning unit support frame 131, a cleaning duct 132, a cleaning duct support frame 133, a cleaning duct accommodating plate 134, a sealing connection pipe, and an online cleaning monitoring apparatus such as a camera. The cleaning duct support frame 133 allows the cleaning duct 132 to extend into the interior of the cooling duct 600. The cleaning unit support frame 131 includes a plurality of support wheels 1311 each abutting against an inner sidewall of the cooling duct 600. The cleaning unit 10 is connected to one end of the cleaning duct 132 extending into the interior of the cooling duct 600, and is moved up and down along the center of the cooling duct 600 by the cleaning unit support frame 131. One end of the sealing connection pipe 135 is connected to the other end of the cleaning duct 132, to guide a cleaning fluid into the cleaning duct 132.

More specifically, as illustrated in FIG. 6, the lifting driving unit of the online cleaning device comprises an electric motor 121, a driving gear 122, a sprocket 123, a belt 124, and a tension gear 125. The electric motor 121 is connected to the driving gear 122, the driving gear 122 is connected to the sprocket 123 via a belt 124, and the sprocket 123 is connected to the cleaning duct accommodating plate 134. The cleaning monitoring and controlling unit 11 is connected to the electric motor 121. The tension gear 125 is located between the sprocket 123 and the driving gear 122, and is connected to the sprocket 123 and the driving gear 122 via the belt 124. Of course, according to the actual need, the skilled persons in the field could also utilize a lifting driving unit with other structures than the particular structure of the lifting driving unit described in the present invention, to complete the lifting driving operation.

Figure 7:
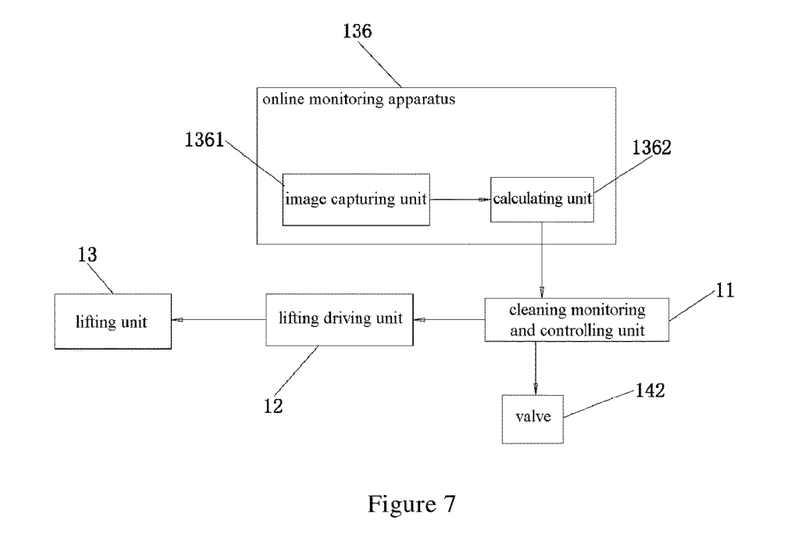
FIG. 7 is a block diagram of a control of an online cleaning device of the invention.

FIG. 7 is a block diagram of a control of an online cleaning device of the present invention. As illustrated in FIG. 7, the online cleaning monitoring apparatus 136 comprises an image capturing unit 1361 and a calculating unit 1362. Herein, the image capturing unit 1361 is arranged on the cleaning unit 10, and is a camera for capturing a real-time image in the cooling duct 600 and transmitting an image signal to the calculating unit 1362. The calculating unit 1362 converts the image signal into a numerical value and compares it with a threshold value, and if the numerical value is higher than the threshold value, a driving signal is transmitted to the cleaning monitoring and controlling unit 11, so as to drive the cleaning unit 10 to carry out a cleaning process.

From the above and in conjunction with FIG. 6 and FIG. 7, the operation processes of the online cleaning device of the present invention are as follows: firstly, the image capturing unit 1361 captures the images in the cooling duct 600 in real-time, and transmits the captured images to the calculating unit 1362; secondly, the calculating unit 1362 converts the captured images into a numerical value and compares it with a threshold value stored in the calculating unit 1362, and if this numerical value is higher than the threshold value, the procedure goes into a cleaning process, but if not, the image capturing unit 1361 continues to capture images; thirdly, the calculating unit 1362 calculates the type of the cleaning fluid necessary for cleaning the cooling duct 600 and transmits a driving signal to the cleaning monitoring and controlling unit 11; in addition, by comparing the obtained numerical value with pollutant threshold values stored in the calculating unit 1362, the calculating unit obtains the kind of the pollutant and at the same time calculates the type of the cleaning fluid for cleaning the corresponding pollutant; then, the cleaning monitoring and controlling unit 11 transmits a stop signal to the dropping system in accordance with the signal transmitted by the calculating unit 1362, and after the drop pill operation stops, the lifting driving unit 12 and the valve 142 are separately driven, such that the cleaning unit 10 is moved from up to down along the central axis of the cooling duct 600 and the cleaning fluid is sprayed; when the cleaning unit 10 moves to the lower part of the cooling duct 600, the cleaning operation ends, the cleaning monitoring and controlling unit 11 separately controls the lifting driving unit 12 and the valve 142, so as to control the cleaning unit 10 to stop spraying and to return to the top of the cooling duct 600, thereafter, the cleaning operation is performed repeatedly until it is clean.

Figure 8:
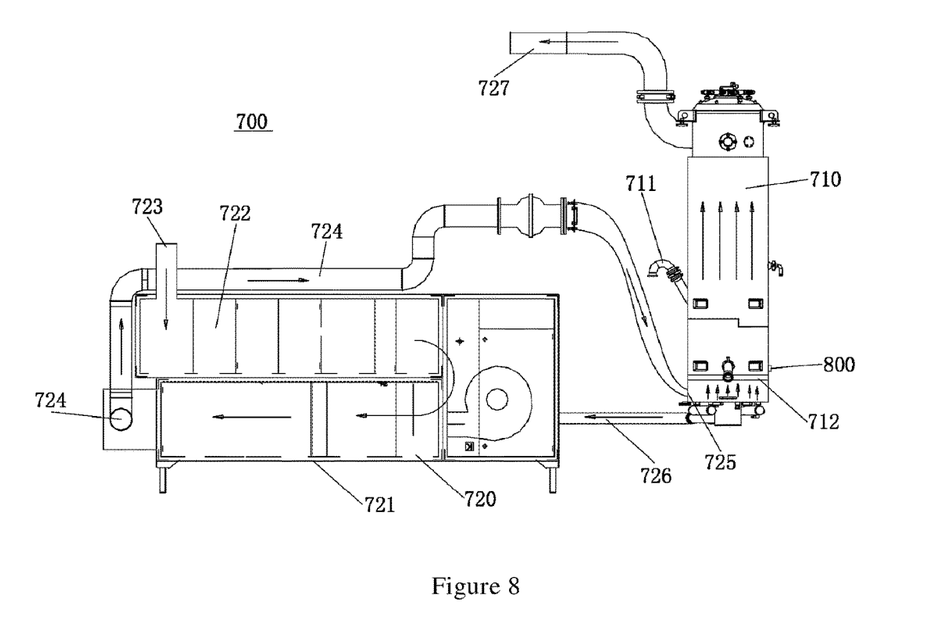
FIG. 8 is a schematic diagram of an overall structure of a fluidized bed of the invention.

FIG. 8 is a schematic diagram of an overall structure of a fluidized bed of the present invention. As illustrated in FIG. 8 and in conjunction with FIG. 1, this air-cooling micro drop pill capsule production line further comprises a fluidized drying and coating system 700 mainly including a fluidized bed 710. The fluidized bed 710 comprises a furnace body at the lower part of which a material feeding inlet 711 is provided, and an end of the cooling duct 600 is connected to the feeding inlet 711 of the fluidized bed 710 via a vacuum duct. The uncoated drop pills subjected to an air-cooling formation are loaded from the feeding inlet 711 under vacuum and transferred into the fluidized bed to be fluidized, dried and coated. Below the feeding inlet 711, an airflow distribution board 712 on which through-holes are arranged is provided. A room-temperature and low-humidity air supply system 720 communicates with the furnace body via a duct, there is an air-in location below the airflow distribution board 712 and air is blown upward. With the through-holes arranged on the airflow distribution board 712, it can not only allow the airflow to pass through, but also effectively prevent the materials inside the furnace body from falling and leaking downward.

The room-temperature and low-humidity air supply system 720 comprises a housing 721 and a low-humidity assembly 722 arranged in the housing. An air inlet 723 and an air-out duct 724 are provided on the housing. Air is subjected to a process by the low-humidity assembly 722 after flowing into the housing from the air inlet 723, and then is input from a furnace body air inlet 725 to the interior of the furnace body via the air-out duct 724, and a fluidized drying process is performed on the materials inside the furnace body with it. Furthermore, the room-temperature and low-humidity air supply system 720 further comprises an air return duct 726 for recycling the airflow, two ends of the air return duct being connected to the furnace body and the housing, respectively. The low-humidity assembly 722 is a combination of a plurality of processing apparatus, successively including a dust removal device, a humidity removal device, an air supply device, a heating device, a filtering device and an efficient filtering device along the airflow direction indicated by an arrow in FIG. 8.

When the fluidized bed operates, at first, materials are loaded under vacuum through the feeding inlet 711 at the lower part of the furnace body, then the gas processed in the processes such as drying, heating, filtering and compressing etc. by the low-humidity assembly 722 is introduced through the furnace body air inlet 725. The processed gas has a humidity of no larger than 5 g/kg, an injection pressure of 1~4 Bar, and a temperature of −20~100° C., preferably 20~60° C. When the materials are dried in a fluidized state to a humidity of 4%, coating is carried out, and afterwards, the materials are unloaded by using a material unloading apparatus such that the products after fluidized drying and coating are output, whereas the waste gas is discharged from an air discharging duct 727.

As required, in general, a drying temperature of the fluidized bed is −20° C.~100° C., and a drying time is 1~4 hours. In order to keep the drop pills in the fluidized state, to solve a problem of adhesion of the drop pills, and meanwhile to improve the production efficiency, the fluidized bed preferably uses a drying method of a gradiently-increased temperature, in which the drop pills are fluidized at −20~30° C., dried at 15~35° C. for 10~120 min, dried at 35~55° C. for 10~60 min and then dried at 55~100° C. for 0~60 min. Most preferably, the drop pills are fluidized at 0~20° C., dried at 25° C. for 60 min, dried at 45° C. for 30 min and then dried at 55° C. for 0~30 min. In order to effectively detect the moisture in the drop pills so as to perform controlling, an online detecting apparatus 800 for monitoring the moisture content and the distribution of particle sizes of the micro pills is further arranged in the fluidized bed. This online moisture detecting apparatus may use an existing detecting element such as a moisture sensor or detector and the like, which will not be described repeatedly herein.

As an all-in-one device with functions of dropping and cooling as well as fluidized drying and coating, the added fluidized drying prevents the problems of adhesion and precipitation of constituents that may occur during the storage of the drop pills prepared by an air-cooling device, moreover, it ensures that the moisture in the drop pills can reach a stable value, and improves uniformity of drug-loading and coating of the device. The heat-molten liquor is injected to be drug-loading coated, which further improves the drug-loading capacity of the drop pills. Also, this device can be used to perform injection to coat the drop pills, so as to satisfy requirements of different processes such as slow-release coating, film coating and sugar coating, etc.

In conjunction with FIG. 1 and FIG. 4, specifically, the operation processes of the present invention are as follows. The liquor is delivered by using the buffer tank 500, and the molten liquor is transferred into the dripper 200 with the thermal insulation cavity. The dripper has an outlet which is in the same direction as the opening at the bottom of the thermal insulation cavity, which guarantees that the liquor can drop out from the bottom of the dripper. By pressure, the mixed liquor flows out from the outlet at the bottom of the dripper 200. According to the size of the drop pills to be required, the pressure or the vibration parameter of the electrodynamic or pneumatic vibration dripper is adjusted, such that the medicine column flowing out from the dripper is cut into medicine drops with required diameter. Herein, the vibration acceleration is 0~110 g (sine acceleration), the vibration amplitude is 0~25.4 mm.

Meanwhile, the gas cooling is started, and the dropped out medicine drops are cooled in the cooling duct 600 due to a low temperature to be solidified as solid particles, and then collected at the lower end of the cooling duct. The upper port of the cooling duct 600 and the opening at the lower end of the thermal insulation cavity of the dripper 200 are communicated with each other in a sealed manner. The lower end of the cooling duct 600 is an opening structure corresponding to a drop pill collecting barrel.

The freezer 41 supplies the generated cooling air into the inner chamber of the cooling duct 600 through the cooling air inlet to circularly rise in the inner chamber, and at the same time, the refrigerant storage tank 51 transfers the refrigerant into the interlayer 610 through the refrigerant inlet, at this moment, the flow direction of the refrigerant in the interlayer 610 is from up to down. Then, the refrigerant enters the inner chamber of the cooling duct 600 through the communicating opening 601 where the interlayer 610 and the cooling duct 600 communicates with each other, and is mixed with the cooling air in the inner chamber of the cooling duct 600 and circularly rise together. When the mixed gas of the refrigerant and the cooling air rises to the top of the cooling duct, the cooling air and the refrigerant are respectively recycled to the freezer 41 and the refrigerant storage tank 51 by the gas recycling apparatus 6, or the mixed gas is discharged to the atmosphere by the gas recycling apparatus 6. For the detailed discharge process, please refer to the foregoing description.

Since the cooling air is directly blown into the cooling duct with a certain angel between the cooling air and the cooling duct 600, the cooling air and the refrigerant forms laminar flow in the cooling duct 600, such that the continuously dropping medicine drops are subjected to a blow of a little gas with a lower temperature and kept at a certain distance from other drops. So, it is possible to avoid adhesion of the drop pills in this region which will influence the subsequent formation.

Subsequently, an end of the cooling duct 600 is connected to a fluidized drying and coating system 700 via a duct, the air supply amount and the air discharging amount are adjusted and the range of temperature is controlled. The small drops after drying are discharged by a vacuum negative pressure, sieved and then enter the fluidized bed again. The air supply amount and the air discharging amount herein are adjusted, and drug-loading coating or film coating is performed according to the requirement of the process. After coating, the device can be also connected to a capsule filling machine to perform filling, and a capsule weight-checking machine is used to check the weight of particle one by one. Therefore, according to a need of practical application, based on the overall structure shown in FIG. 1, the air-cooling micro drop pill capsule production line provided by the present invention may be also provided with a capsule filling machine and a capsule weight-checking apparatus. These two apparatus belong to the related art and will not be described herein again.

Hereinafter, the devices of the present invention will be further described in detail by the way of the best examples. These examples are used merely to explain the present invention, without any limitation to the scope of the present invention.

Example 1 Preparation of the Compound *Salvia Miltiorrhiza* Drop Pills (1) Material melting step: 600 g of *Salvia Miltiorrhiza* and *Panax Notoginseng* extract, 5 g of borneol, and 2000 g of polyethylene glycol 6000 (PEG-6000) auxiliary material were prepared; the PEG-6000 was firstly added into a molten material tank and heated to 90° C. to pre-melt, into which the *Salvia Miltiorrhiza* and *Panax Notoginseng* extract was then added, and the resultant materials were fed into a homogenizer to be mixed homogenously at 5000 rpm for 200 min; next, the resultant materials were molten homogenously at 10000 rpm for 100 min at a temperature of 100° C. to obtain a uniformly mixed liquid.

(2) Dropping step: a vibration frequency of a pneumatic-vibrated dripper was adjusted to 300 Hz and a thermal insulation chamber used a steam jacket for heat preservation, the temperature was controlled at 200° C., a dropping speed was matched with a material melting rate in Step (1), a dropping pressure was 3 Bar, the dropping speed was 10 kg/hr and a dropping acceleration was 1 G.

(3) Condensation step: air was supplied into the molten material tank by an air pump via a pipeline; the aforesaid molten liquid was delivered to flow into a dripper and dropped out from the bottom of the dripper into a cooling duct that is vertical to the ground; cooling air was started to reach a cooling temperature of −120° C., the cooling air inlet formed an angle of 30° with the horizontal plane; and the cooling air was allowed to flow circularly in the cooling duct, such that the dropped out liquor drops were cooled and solidified to solid drop pills in the cooling duct; a duct at the lower end of the cooling duct was connected to a section of a fluidized bed for fluidized drying and drug-loading coating.

(4) Drying step: the resultant drop pills were dried in a fluidized state to be drug-loading coated. After the drop pill materials formed a good fluidization state in the bed body at a temperature of −20° C.~30° C., the temperature was increased to 50° C. to dry for 2 hours; the moisture content of the uncoated drop pills was controlled at 5.0% to obtain an intermediate uncoated drop pills.

(5) Coating step: the usage of coating powder was calculated based on the coating feed capacity and the prescription, a coating liquid with a concentration of 10% was prepared and stirred for 45 min. The inlet air temperature was initially set to 40° C., and after the qualified drop pills were fed into the fluidized bed, the set inlet air temperature was increased to 48° C., and when the temperature of the drop pill materials reached 38° C., the coating was started. The temperature of the drop pill materials was controlled at 35~45° C. during the coating, and decreased to 30° C. or lower after the coating was ended. The resultant drop pills were discharged, and eventually, drop pills with a particle size of 2.0 mm were obtained by sieving.

Example 2 Preparation of the *Salvia Miltiorrhiza* Drop Pills (1) Material melting step: 600 g of *Salvia Miltiorrhiza* extract was prepared, then into which 60 g of water and 1500 g of polyethylene glycol 6000 auxiliary material were added; the resultant materials were put into a molten material tank and heated to 90° C., and then were mixed by a low-speed homogenization (3200 rpm); after this mixing, the homogenization speed was increased to 5000 rpm to melt the material for 6 min; at last, the resultant materials were completely molten and mixed uniformly into liquid.

(2) Dropping step: a vibration frequency of a pneumatic vibration dripper was adjusted to 50 Hz and a thermal insulation chamber used infrared ray heating for heat preservation, the temperature was controlled at 70° C., a dropping pressure was 4 Bar, a dropping speed was 40 kg/hr and a dropping acceleration was 3 G.

(3) Condensation step: air was supplied into the molten material tank by an air pump via a pipeline, the aforesaid uniformly molten liquid was delivered to flow into the dripper and dropped out from the bottom of the dripper into a cooling duct under a dropping pressure of 0.18 MPa; while the aforesaid liquid was dropping out, the cooling air was started to reach a cooling temperature of −10° C.; the cooling air was allowed to flow circularly in the cooling duct, and the cooling air inlet formed an angle of 45° with the horizontal plane; the liquor drops dropped out from the dripper were cooled and solidified to solid drop pills in the cooling duct, a duct at a lower end of the cooling duct was connected to a section of a fluidized bed.

(4) Fluidization step: the resultant drop pills were dried in a fluidized state to be drug-loading coated. After the drop pill materials formed a good fluidization state in the bed body, the temperature was increased to 25° C. to dry for 60 min, further increased to 45° C. to dry for 30 min, still further increased to 55° C. to dry for 30 min, and then deceased to 30° C. or lower to discharge the resultant drop pills. The moisture content of the uncoated drop pills was controlled at 3.0~7.0% to obtain an intermediate uncoated drop pills.

(5) Coating step: the usage of coating powder was calculated based on the coating feed capacity and the prescription, a coating liquid with a concentration of 18% was prepared and stirred for 45 min. The inlet air temperature was initially set to 25° C., and after the qualified drop pills were fed into the fluidized bed, the set inlet air temperature was increased to 48° C.; and when the temperature of the drop pill materials reached 38° C., the coating was started. The temperature of the drop pill materials was controlled at 35~45° C. during the coating, and decreased to 30° C. or lower after the coating was ended. The resultant drop pills were discharged, and eventually, drop pills with a particle size of 1.0~2.0 mm were obtained by sieving.

Example 3 Preparation of the Compound *Salvia Miltiorrhiza* Drop Pills (1) Material melting step: 600 g of *Salvia Miltiorrhiza* and *Panax Notoginseng* extract, 5 g of borneol, and 2000 g of polyethylene glycol 6000 auxiliary material were prepared. The polyethylene glycol was firstly added into a molten material tank and heated to 80° C. to pre-melt, into which the *Salvia Miltiorrhiza* and *Panax Notoginseng* extract was then added, and the resultant materials were fed into a homogenizer to be mixed homogenously at 2500 rpm for 100 min; next, the resultant materials were molten homogenously at 6000 rpm for 20 min with a temperature of 100° C. to obtain a uniformly mixed liquid.

(2) Dropping step: a vibration frequency of a pneumatic vibration dripper was adjusted to 90 Hz, a dropping acceleration was 3.5 G, a dropping speed was 12 kg/hr, a dropping pressure was 1.0 Bar; a thermal insulation chamber used a steam jacket for heat preservation and the temperature was controlled at 70° C.

(3) Condensation step: air was supplied into a molten material tank by an air pump via a pipeline, the aforesaid molten liquid was delivered to flow into the dripper and dropped out from the bottom of the dripper into a cooling duct which is vertical to the ground; the cooling air was started to reach a cooling temperature of −100° C.; the cooling air inlet formed an angle of 90° with the horizontal plane, and the cooling air was allowed to flow circularly in the cooling duct, such that the dropped out liquor drops were cooled and solidified to solid drop pills in the cooling duct.

A duct at a lower end of the cooling duct was connected to a section of a fluidized bed for fluidized drying and drug-loading coating. Specifically, the resultant materials would form a fluidization state at a temperature of 20° C., then would be dried at 25° C. for 60 min, dried at 45° C. for 30 min and at last dried at 55° C. for 30 min.

Example 4 Preparation of the Compound *Salvia Miltiorrhiza* Drop Pills (1) Material melting step: the compound *Salvia Miltiorrhiza* extract was prepared, which and a mixture of arabic gum and lactose (in a ratio of 1:1) were fed into a homogenizer to be mixed homogenously at 5000 rpm for 200 min; then the resultant materials were molten homogenously at 10000 rpm for 100 min with a temperature of 100° C. to obtain an intermediate material liquid.

(2) Dropping step: the intermediate material liquid was dropped through the dripper by vibration at a vibration frequency of 200 Hz and a dripper's temperature of 100° C. under a dropping pressure of 4.0 Bar; a dropping speed was matched with the material melting rate in Step (1), and the dropping speed was 15 kg/hr.

(3) Condensation step: the dropped out medicine drops were cooled rapidly in a cooling gas and solidified to uncoated drop pills having a diameter of 4.0 mm, the temperature of the cooling gas was −300° C.

A duct at a lower end of the cooling duct was connected to a section of a fluidized bed for fluidized drying and drug-loading coating. Specifically, the resultant materials would form a fluidization state at a temperature of 0° C., then would be dried at 25° C. for 60 min, dried at 45° C. for 30 min and at last dried at 55° C. for 30 min.

Example 5 Preparation of the Compound *Salvia Miltiorrhiza* Drop Pills 75 g of compound *Salvia Miltiorrhiza* extract, 7.5 g of borneol, and 165 g of lactitol were prepared. The compound *Salvia Miltiorrhiza* micro drop pills were prepared with the following method:

(1) Material melting step: the compound *Salvia Miltiorrhiza* extract and the lactitol were fed into a homogenizer to be mixed homogenously at 2500 rpm for 100 min; then the resultant materials were molten homogenously at 6000 rpm for 50 min with a temperature of 80° C. to obtain an intermediate material liquid;

(2) Dropping step: the intermediate material liquid was dropped through the dripper by vibration at a vibration frequency of 130 Hz and a the dripper's temperature of 140° C. under a dropping pressure of 1.8 Bar; a dropping speed was matched with the material melting rate in Step (1), and the dropping speed was 25 kg/hr;

(3) Condensation step: the dropped out medicine drops were cooled rapidly in a cooling gas and solidified to uncoated drop pills having a diameter of 1 mm, the temperature of the cooling gas was −100° C.

(4) Drying step: the resultant drop pills were dried by using a fluidized drying device at −20° C. for 4 hours to obtain the dried uncoated drop pills.

(5) Coating step: the dried uncoated drop pills were coated in a fluidized bed to obtain the coated drop pills; herein the ratio of the coating material to the uncoated drop pill was 1:25 by weight, the concentration of the coating liquid was 10% and the coating temperature was 40° C.

Example 6 Preparation of the Compound *Salvia Miltiorrhiza* Drop Pills 75 g of compound *Salvia Miltiorrhiza* extract, 7.5 g of borneol, and 165 g of polyethylene glycol 8000 were prepared. The compound *Salvia Miltiorrhiza* micro drop pills were prepared with the following method:

The powder of the compound *Salvia Miltiorrhiza* extract was added with water and stirred at 60° C. for 10 min or longer to obtain a pre-mixed material of medicine.

(1) Material melting step: the compound *Salvia Miltiorrhiza* extract and the polyethylene glycol 8000 were fed into a homogenizer to be mixed homogenously at 2500 rpm for 100 min; then the resultant materials were molten homogenously at 6000 rpm for 50 min with a temperature of 80° C. to obtain an intermediate material liquid;

(2) Dropping step: the intermediate material liquid was dropped through the dripper by vibration at a vibration frequency of 140 Hz and a dripper's temperature of 100° C. under a dropping pressure of 0.5 Bar; a dropping speed was matched with the material melting rate in Step (1), and the dropping speed was 30 kg/hr;

(3) Condensation step: the dropped out medicine drops were cooled rapidly in a cooling gas and solidified to uncoated drop pills having a diameter of 2 mm, the temperature of the cooling gas was −100° C.

(4) Drying step: the resultant drop pills were dried by using a fluidized drying device at 100° C. for 1 hour to obtain the dried uncoated drop pills.

(5) Coating step: the dried uncoated drop pills were coated in a fluidized bed to obtain the coated drop pills; herein, the ratio of the coating material to the uncoated drop pill was 1:25 by weight, the concentration of the coating liquid was 10% and the coating temperature was 40° C.

Example 7 Preparation of the Compound *Salvia Miltiorrhiza* Drop Pills 90 g of compound *Salvia Miltiorrhiza* extract, 12 g of borneol, and 270 g of polyethylene glycol 1000 were prepared. The compound *Salvia Miltiorrhiza* micro drop pills were prepared with the following method:

The powder of active pharmaceutical ingredients of compound *Salvia Miltiorrhiza* was added with water and stirred at 30° C. for 10 min or longer to obtain a pre-mixed material of medicine.

(1) Material melting step: the compound *Salvia Miltiorrhiza* extract and the polyethylene glycol 1000 were fed into a homogenizer to be mixed homogenously at 2500 rpm for 100 min; then the resultant materials were molten homogenously at 6000 rpm for 20 min with a temperature of 100° C. to obtain an intermediate material liquid;

(2) Dropping step: the intermediate material liquid was dropped through the dripper by vibration at a vibration frequency of 100 Hz, a dropping acceleration of 1 G, a dropping speed of 10 Kg/hr and the dripper's temperature of 75° C. under a dropping pressure of 1.0 Bar.

The dropping speed was matched with the material melting rate in Step (1);

(3) Condensation step: the dropped out medicine drops were cooled rapidly in a cooling gas and solidified to uncoated drop pills having a diameter of 1.5 mm, the temperature of the cooling gas was −80° C.

(4) Drying step: the resultant drop pills were dried by using a drying method of a gradiently-increased temperature. Specifically, the resultant drop pills formed a fluidization state at a temperature of −20° C., dried at 15° C. for 10 min, and then dried at 35° C. for 10 min to obtain the dried uncoated drop pills.

(5) Coating step: the dried uncoated drop pills were coated in a fluidized bed to obtain the coated drop pills; herein, the ratio of the coating material to the uncoated drop pill was 1:25 by weight, the concentration of the coating liquid was 10% and the coating temperature was 40° C.

Example 8 Preparation of the Compound *Salvia Miltiorrhiza* Drop Pills 100 g of compound *Salvia Miltiorrhiza* extract, 5 g of borneol, and 35 g of a mixture of polyethylene glycol 4000 and polyethylene glycol 6000 (in a ratio of 1:1) were prepared. The compound *Salvia Miltiorrhiza* micro drop pills were prepared with the following method:

The powder of the Compound *Salvia Miltiorrhiza* extract was added with water and stirred at 80° C. for 10 min or longer to obtain a pre-mixed material of medicine.

(1) Material melting step: the compound *Salvia Miltiorrhiza* extract and the mixture of the polyethylene glycol 4000 and the polyethylene glycol 6000 (1:1) were fed into a homogenizer to be mixed homogenously at 2500 rpm for 100 min; then the resultant materials were molten homogenously at 6000 rpm for 80 min at a temperature of 80° C. to obtain an intermediate material liquid;

(2) Dropping step: the intermediate material liquid was dropped through the dripper by vibration at a vibration frequency of 200 Hz, a dropping acceleration of 20 G, a dropping speed of 40 Kg/hr and the dripper's temperature of 85° C. under a dropping pressure of 3.0 Bar.

The dropping speed was matched with the material melting rate in Step (1);

(3) Condensation step: the dropped out medicine drops were cooled rapidly in a cooling gas and solidified to uncoated drop pills having a diameter of 0.5 mm, the temperature of the cooling gas was 120° C.

(4) Drying step: the resultant drop pills were dried by using a drying method of a gradiently-increased temperature, in which: the resultant drop pills formed a fluidization state at a temperature of 30° C., dried at 35° C. for 120 min, then dried at 55° C. for 60 min and at last dried at 100° C. for 60 min to obtain the dried uncoated drop pills.

(5) Coating step: the dried uncoated drop pills were coated in a fluidized bed to obtain the coated drop pills; herein, the ratio of the coating material to the uncoated drop pill was 1:25 by weight, the concentration of the coating liquid was 10% and the coating temperature was 40° C.

In conclusion, the present invention employs a vibration shear dropping method, which can improve the formation speed of drop pills and the roundness of drop pills, and can reduce a difference in weights of drop pills. A real-time monitoring is carried out when the dropping is performed, such that the production yield of the drop pills can be increased by adjusting each of the parameters. The present invention realizes a method of preparing drop pills by using an air cooling manner, in which the drug-loading capacity can be improved while the micro pills can be dropped at a high speed, and in which the usage of auxiliary materials and the dosage can be greatly reduced. The present invention can avoid any residual organic solvent which occurs in a traditional liquid cooling manner. The present invention effectively eliminates the disadvantages existing in a traditional drop pill apparatus, and really achieves advantages of low power consumption, high speed, high efficiency and high drug-loading capacity. Moreover, the present invention has a wider droppable range and greatly improves the production rate and dropping effects.

What is claimed is:

1. An air-cooling micro drop pill capsule production line comprising a drop pill system, an air-cooling circulation system and a control system, the drop pill system comprising a molten material tank and a dripper connected thereto, a vibration apparatus which drives the dripper to vibrate up and down is arranged between the molten material tank and the dripper, the vibration apparatus configured to generate a vibration shear force which cuts liquor flowing out from the dripper into drops, and forms drop pills after the drops fall into the air-cooling circulation system and are cooled, an online monitoring apparatus arranged on the dripper, and comprising a pulse signal emission mechanism with an emission frequency which is the same as a vibration frequency of the vibration apparatus, the control system configured to control and regulate a dropping parameter according to a monitoring result of the online monitoring apparatus, the air-cooling circulation system comprising a cooling duct and a refrigerating apparatus connected to the cooling duct configured to refrigerate the cooling duct, wherein an interlayer is arranged outside the cooling duct and a lower part of the interlayer is configured to communicate with an interior of the cooling duct;

the refrigerating apparatus comprising a cooling air refrigerating apparatus and a cold trap refrigerating apparatus, wherein the cooling air refrigerating apparatus comprises a freezer, an air outlet of the freezer and a cooling air inlet of the cooling duct being communicated with each other such that cooling air rises circularly in an inner chamber of the cooling duct;

wherein the cold trap refrigerating apparatus comprises: a refrigerant storage tank containing a refrigerant, a refrigerator refrigerating the refrigerant in the refrigerant storage tank, and a heat exchanger, a refrigerant outlet of the refrigerant storage tank being connected to a refrigerant inlet arranged on an upper part of the interlayer such that the refrigerant is transferred into the interlayer through the refrigerant inlet, then transferred from the upper part of the interlayer to the lower part of the interlayer and then to the inner chamber of the cooling duct; the refrigerant configured to rise circularly together with the cooling air in the inner chamber of the cooling duct simultaneously, and then be discharged or recycled through a top of the cooling duct the air-cooling circulation system further comprising a gas recycling apparatus including a first valve, a second valve, a gas recycling machine and a separator, one end of a duct controlled by the first valve being configured to communicate with the cooling duct, and another end thereof being configured to communicate with atmosphere; one end of a duct controlled by the second valve being configured to communicate with the cooling duct, and another end thereof being connected to the separator via the gas recycling machine;

the gas recycling machine further including a gas discharging pipe, a vortex blower, a gas recycling pipe and a gas recycling box, and when the second valve is opened, the vortex blower operates to extract gas in the cooling duct through the gas discharging pipe and to discharge gas collected by extraction into the gas recycling box through the gas recycling pipe.

2. The air-cooling micro drop pill capsule production line according to claim 1, wherein the online monitoring apparatus is arranged on a lower side face of the dripper; and the pulse signal emission mechanism is a stroboscopic lamp with the emission frequency which is the same as the vibration frequency of the vibration apparatus.

3. The air-cooling micro drop pill capsule production line according to claim 2, wherein the online monitoring apparatus further includes a camera arranged corresponding to the stroboscopic lamp, the camera is positioned on the same horizontal plane as the stroboscopic lamp and forms an angle of 15°~145° with an illumination path of the stroboscopic lamp.

4. The air-cooling micro drop pill capsule production line according to claim 3, wherein the dripper comprises a dropping plate on which a plurality of drip holes are provided, a concave annular groove is arranged at the periphery of the drip hole; and the concave annular groove has an inner diameter equaling to an inner diameter of the drip hole plus 0.4 mm, an outer diameter of 1.5 mm or larger, and a depth of 0.5~5 mm.

5. The air-cooling micro drop pill capsule production line according to claim 2, wherein the dropping parameters comprise:
the emission frequency of the stroboscopic lamp and the vibration frequency of the vibration apparatus: 50~300 HZ;
a dropping speed: 10~40 Kg/hr;
a dropping acceleration: 1~20 G;
a dropping pressure: 0.5~4.0 Bar; and
the dripper's temperature: 70~200° C.

6. The air-cooling micro drop pill capsule production line according to claim 5, wherein one or more of the dropping parameters are in a range of:
the emission frequency of the stroboscopic lamp and the vibration frequency of the vibration apparatus: 90~200 Hz;
a dropping speed: 12~30 Kg/hr;
a dropping acceleration: 3~10 G;
a dropping pressure: 1.0~3.0 Bar; and
the dripper's temperature: 70~100° C.

7. The air-cooling micro drop pill capsule production line according to claim 6, wherein one or more of the dropping parameters are in a range of:
the emission frequency of the stroboscopic lamp and the vibration frequency of the vibration apparatus: 130~140 HZ;
a dropping speed: 15~25 Kg/hr;
a dropping acceleration: 3.5~4.5 G;
a dropping pressure: 1.8 Bar; and
the dripper's temperature: 75~85° C.

8. The air-cooling micro drop pill capsule production line according to claim 1, wherein the cooling duct is a straight barrel-shaped or spiral-shaped duct with a length of 5~10 m.

9. The air-cooling micro drop pill capsule production line according to claim 8, wherein an online cleaning device is arranged on the cooling duct and comprises a cleaning unit, a controlling unit, a lifting driving unit and a lifting unit,
the controlling unit configured to drive the lifting unit with the lifting driving unit so as to drive the cleaning unit to move up and down,
the lifting unit is arranged outside of the top of the cooling duct in the air-cooling circulation system.

10. The air-cooling micro drop pill capsule production line according to claim 9, wherein the lifting unit comprises a cleaning unit support frame, a cleaning duct, a cleaning duct support frame, a cleaning duct accommodating plate and a sealing connection pipe;
the cleaning duct support frame configured to allow the cleaning duct to extend into the interior of the cooling duct;
the cleaning unit support frame includes a plurality of support wheels each abutting against an inner sidewall of the cooling duct,
the cleaning unit is connected to one end of the cleaning duct extending into the interior of the cooling duct, and is moved up and down along the center of the cooling duct by the cleaning unit support frame; and
one end of the sealing connection pipe is connected with the other end of the cleaning duct, to guide a cleaning fluid into the cleaning duct.

11. The air-cooling micro drop pill capsule production line according to claim 10, wherein the lifting unit further comprises an online monitoring apparatus which includes an image capturing unit and a calculating unit, wherein the image capturing unit is arranged on the cleaning unit to capture a real-time image in the cooling duct and transmit an image signal to the calculating unit, and wherein the calculating unit converts the image signal into a numerical value and compares it with a threshold value, and if the numerical value is higher than the threshold value, a driving signal is transmitted to the controlling unit so as to drive the cleaning unit to perform a cleaning process.

12. The air-cooling micro drop pill capsule production line according to claim 10, wherein the fluidized bed further includes an online detecting apparatus configured to monitor moisture content and distribution of particle sizes of micro pills.

13. The air-cooling micro drop pill capsule production line according to claim 8, wherein the cooling duct is a straight barrel-shaped or spiral-shaped duct with a length of 6 m.

14. The air-cooling micro drop pill capsule production line according to claim 1, wherein the air-cooling micro drop pill capsule production line further comprises a fluidized drying and coating system which includes a fluidized bed, wherein an end of the cooling duct is connected to an inlet of the fluidized bed via a vacuum duct, the air-cooling micro drop pill capsule production line configured to subject uncoated drop pills to an air-cooling formation to be loaded under vacuum and transferred into the fluidized bed to be fluidized, dried and coated;
the fluidized bed comprises a furnace body below a material feeding inlet, below the feeding inlet is an airflow distribution board, a bottom of the airflow distribution board is communicated with an air-out duct of a room-temperature and low-humidity air supply system configured to supply a room-temperature and low-humidity air into the furnace body of the fluidized bed via the air-out duct, and perform a fluidization drying process on materials inside the furnace body;
the room-temperature and low-humidity air supply system comprises a housing on which an air-in duct and the air-out duct are provided and a low-humidity assembly arranged in the housing, configured to subject air to a process by the low-humidity assembly after flowing into the housing from the air-in duct, and then input into the furnace body through the air-out duct;
the room-temperature and low-humidity air supply system further comprises an air return duct configured to recycle the airflow, two ends of the air return duct being connected to the furnace body and the housing, respectively.

15. The air-cooling micro drop pill capsule production line according to claim 14, wherein the low-humidity assembly includes a plurality of devices in series, successively including a dust removal device, a humidity removal device, an air supply device, a heating device, and a filtering device along a flowing direction of the airflow.

16. The air-cooling micro drop pill capsule production line according to claim 15, wherein a drying temperature of the fluidized bed is in a range of −20° C.~100° C., and a drying time thereof is in a range of 1~4 hours.

17. The air-cooling micro drop pill capsule production line according to claim 16, wherein the fluidized bed is configured to use preferably use a drying method of a gradiently-increased temperature, in which the drop pills are fluidized at −20~30° C., dried at 15~35° C. for 10~120 min, dried at 35~55° C. for 10~60 min, and then dried at 55~100° C. for 0~60 min.

18. The air-cooling micro drop pill capsule production line according to claim 17, wherein the fluidized bed is configured to use the drying method of a gradiently-increased temperature, in which the drop pills are fluidized at 0~20° C.

19. The air-cooling micro drop pill capsule production line according to claim 18, wherein the fluidized bed is configured to use the drying method of a gradiently-increased temperature, in which the drop pills are further dried at 25° C. for 60 min, dried at 45° C. for 30 min, and then dried at 55° C. for 0~30 min.

* * * * *